United States Patent [19]
Durham

[11] Patent Number: 6,162,228
[45] Date of Patent: Dec. 19, 2000

[54] DEVICE FOR MAGNETICALLY TARGETING LOCKING HOLES IN ORTHOPEDIC HARDWARE

[76] Inventor: Alfred A. Durham, 2954 Lockridge Rd., Roanoke, Va. 24014

[21] Appl. No.: 09/357,245

[22] Filed: Jul. 20, 1999

[51] Int. Cl.[7] .................................................... A61B 17/58
[52] U.S. Cl. ............................................................. 606/96
[58] Field of Search ................... 606/96, 97, 98, 606/87, 95, 62–64; 33/286, 263, 334

[56] References Cited

U.S. PATENT DOCUMENTS

| | | | |
|---|---|---|---|
| 4,621,628 | 11/1986 | Brudermann | 606/97 |
| 5,049,151 | 9/1991 | Durham et al. | |
| 5,127,913 | 7/1992 | Thomas, Jr. | 606/95 |
| 5,411,503 | 5/1995 | Hollstien et al. | 606/96 |
| 5,433,720 | 7/1995 | Faccioli et al. | 606/98 |
| 5,540,691 | 7/1996 | Elstrom et al. | 606/98 |
| 5,584,838 | 12/1996 | Rona et al. | 606/96 |
| 5,693,054 | 12/1997 | Durham et al. | |
| 5,707,375 | 1/1998 | Durham et al. | |

*Primary Examiner*—Jeffrey A. Smith
*Assistant Examiner*—Eduardo C. Robert
*Attorney, Agent, or Firm*—Larson & Taylor, PLC

[57] ABSTRACT

A device is provided for targeting transverse locking holes for locking screws or pins in an elongate hollow orthopedic locking rod. Such rods are inserted into the intramedullary canal of a bone of a patient that is being fixed in place by the rod. The device includes a tubular drill guide member having a drill guide bore therethrough for receiving a drill. The drill, when aligned with a target locking hole, is used in drilling through the bone via the target locking hole. The guide member has a distal end adapted to be brought into contact with the bone. A target magnet or magnet assembly is inserted into the longitudinal bore in the locking element to a position adjacent to, and proximally offset from, the target locking hole. A magnetic targeting unit is mounted for movement on the drill guide member in laterally offset relation to the drill guide bore. The unit is used to sense the location of the target magnet and produces an output (e.g., a light or buzzer signal) when the magnetic targeting unit is aligned with the target magnet and thus the drill guide bore is aligned with the target locking hole.

24 Claims, 6 Drawing Sheets though the devices and methods disclosed in these patents represent important advances in the art, the requirement for such a guide wire or pin complicates the procedure.

DEVICE FOR MAGNETICALLY TARGETING LOCKING HOLES IN ORTHOPEDIC HARDWARE

FIELD OF THE INVENTION

The present invention relates to devices and arrangements for positioning locking screws or pins for orthopedic hardware and such as interlocking rods and more particularly, to an improved device for locating or targeting the locking holes in such hardware to enable proper positioning of such screws or pins.

BACKGROUND OF THE INVENTION

Orthopedic hardware that is inserted in an intramedullary manner has become an increasingly useful aid in treating fractures of long bones (e.g. the femur or tibia). In a typical application, an interlocking rod or bar, commonly referred to as a "nail," is inserted into a femur and transverse screws or pins are used to fix the rod in place in the bone. These screws or pins are screwed or otherwise inserted from the outside of the limb or other body part through the adjacent bone wall into distal and transverse screw holes in the locking rod.

The use of such locking screws to ensure that the rod is fixed firmly in place has extended the range of such orthopedic aids and appliances well beyond that of the original locking rods without such transverse screws. However, the problem of properly inserting the screws from the outside of the limb is a different one. In this regard, it is noted that such locking rods are long enough that the rods will bend when installed and thus locking or positioning devices which are aligned or centered based on a reference taken from the top of the rod have been ineffective in precisely locating the transverse screw holes. It will be understood that the locking screws or pins must be precisely located so that the load on the limb involved is transmitted, during healing, through the transverse screws or pins and the associated locking rod and not through the broken portion of the bone.

One method that is capable of providing precise locating of the transverse distal holes in locking rods uses x-rays. However, long periods of x-ray exposure are required and the need to move the x-ray equipment into and out of position to check the screw or pin location means that there is a risk of a loss of alignment each time that the equipment is moved. As a consequence, the positioning of such locking screws or pins is typically the most time consuming and difficult portion of the overall rod implantation procedure.

In addition to x-rays, a number of different approaches have been taken in an attempt to find a safe, effective and rapid way of inserting transverse locking screws and pins into locking rods. Reference is made to U.S. Pat. No. 5,049,151 (Durham et al), U.S. Pat. No. 5,514,145 (Durham et al) and U.S. Pat. No. 5,707,375 (Durham et al) for a further discussion of these prior art approaches. A further approach involves a computer driven image of stacked magnetic coils which sense a magnetic field. One serious limitation of the latter approach concerns the fact that most locking rod systems will not accept a magnet that is placed at the screw hole.

As described therein, the systems disclosed in the above-mentioned U.S. Pat. Nos. 5,049,151, 5,514,145 and 5,707, 375 involve the use of a pivotable magnetic positioning device in positioning a guide wire or pin over which a cannulated drill is passed so as to then permit the drill to drill a hole through the bone in alignment with the screw hole after the locating magnet is removed from the rod. Although the devices and methods disclosed in these patents represent important advances in the art, the requirement for such a guide wire or pin complicates the procedure.

SUMMARY OF THE INVENTION

In accordance with the invention, a magnetic targeting device is provided which enables drilling directly through the target locking hole thereby eliminating the need for a guide wire or pin such as used in the prior art, as indicated above, in the prior art, cannulated drill element would be used to drill over the guide wire or pin in drilling through the locking hole after the target magnet was removed from the hole location. Among other general advantages, the device of the invention provides distal targeting without x-rays, is inexpensive and operates percutaneously. Further advantages are as described below.

According to the invention, a device is provided for targeting transverse locking holes for locking screws or pins in a hollow orthopedic locking element or rod, the locking element further including a longitudinal bore and being inserted, in use, within a bone of a patient to fix the bone, and the device comprising: a tubular drill guide member having a drill guide bore therethrough for receiving a drill for, when aligned with a target locking hole, drilling through the bone via the target locking hole, the guide member having a distal end adapted to be brought into contact with the bone; at least one target magnet adapted to be inserted into the longitudinal bore in the locking element to a position adjacent to, and proximally offset from, the target locking hole; and magnetic targeting means, mounted for movement on the drill guide member in laterally offset relation to the drill guide bore, for sensing the location of the at least one target magnet and for producing an output when said magnetic targeting means is aligned with the at least one target magnet and thus the drill guide bore is aligned with the target locking hole.

Preferably, the device further comprises a movable sleeve which is mounted on the guide member, which carries the magnetic targeting means, and which is movable to a position wherein the magnetic targeting means is brought into contact with an area of skin overlying the bone.

Advantageously, a spline connection is provided between the sleeve and the drill guide member for preventing rotation of the sleeve on the drill guide member.

The distal end of said drill guide member preferably includes teeth for holding the drill guide member in contact with the bone.

In one embodiment, the magnetic targeting means comprises a magnetic balance finder having a movable element which assumes a predetermined orientation when aligned with the at least one target magnet. The magnetic targeting means preferably comprises a magnetic compass having a movable pointer, a sensor for sensing the position of the pointer and for producing a trigger signal when the pointer assumes a predetermined position, and an indicator device activated by the trigger signal. The sensor advantageously comprises a magnetic switch. The indicator device advantageously comprises an indicator lamp or a buzzer. Preferably, the magnetic targeting means further comprises a control handle affixed to the drill guide member. The at least one target magnet preferably comprises a target magnet located at the distal end of a wand member.

In an advantageous implementation, the magnetic targeting means further comprises an alignment arm extending transverse to the drill guide member for assisting in providing preliminary alignment of the magnetic targeting means. The orthopedic locking element advantageously includes a U-shaped handle having an external leg extending substantially parallel to the longitudinal bore in the locking element and an axial alignment element extending axially from the external arm for alignment with the alignment arm.

In accordance with a further embodiment of the invention, the magnetic targeting means comprises a magnetic switch for producing a triggering signal when the magnetic switch is in alignment with the at least one target magnet. In an alternative implementation of this embodiment, the at least one target magnet comprises first and second spaced magnet devices for producing respective magnetic fields, and the magnetic targeting means comprises a first, x-axis magnetic switch for detecting the magnetic field produced by the first magnet device and a second, y-axis magnetic switch for sensing the magnetic field produced by the second magnet device. Preferably, the at least one target magnet comprises at least one pair of adjacently disposed magnets for producing a resultant magnetic field, and the magnetic targeting means comprises at least one magnetic switch for producing a triggering signal response to detecting a predetermined characteristic of the resultant magnetic field. In one implementation, the at least one pair of magnets comprises first and second permanent magnets of opposite polarity disposed in side by side relation. In another implementation, the at least one pair of magnets comprises first and second magnets of like polarity disposed in side by side relation. In yet another implementation, the at least one pair of magnets comprises first and second permanent magnets of opposite polarity disposed in side by side relation and third and fourth permanent magnets of like polarity disposed in side by side relation and spaced from the first and second magnets.

Advantageously, the device further comprises a movable sleeve mounted on said drill guide member, carrying one or more magnetic switches and movable to a position wherein the magnetic switch is brought into contact with an area of skin overlying the bone.

In yet another embodiment, the magnetic targeting means comprises a sensor magnet and a strain gauge for sensing the torque exerted on the sensor magnet by the target magnet.

In accordance with a further aspect of the invention, a device is provided for targeting transverse locking holes in a hollow elongate orthopedic locking element including a longitudinal bore therein and adapted to be located, in use, within a bone of a patient, and thereby enabling locking screws to be inserted into the locking holes, the device comprising: a target magnet adapted to be inserted into the locking element at a target locking hole; and a cannulated targeting magnet including a rounded bottom surface about which the targeting magnet can pivot and adapted to be placed, in use, into pivotable contact with a surface of the bone so as to be brought into alignment with the target magnet, the cannulated targeting magnet having a drill guide passage therethrough for receiving a drill for, when the targeting magnet is aligned with the target magnet at the target locking hole, drilling through the bone via the target locking hole.

Further features and advantages of the present invention will be set forth in, or apparent from, the detailed description of preferred embodiments thereof which follows.

DESCRIPTION OF THE PREFERRED EMBODIMENTS

Figure 1:
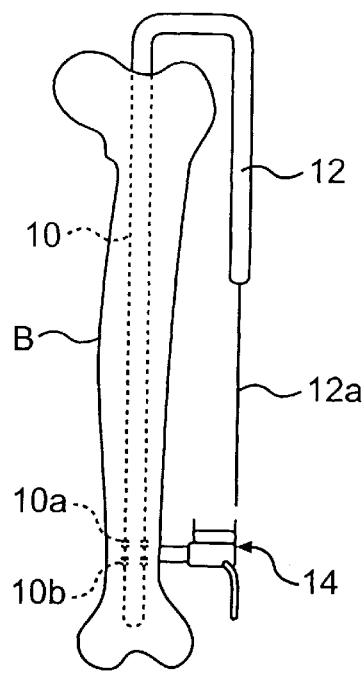
FIG. 1 is a side elevational view of a bone with an intramedullary rod therein, showing, in a schematic manner, the magnetic positioning guide device of one preferred embodiment of the invention.

Referring to FIG. 1, there is shown a long bone B with an intramedullary interlocking rod 10 implanted therein. A U-shaped insertion handle 12 for rod 10 includes an external portion that terminates in an alignment rod 12a which parallels on the outside of the bone B the bend of locking rod 10. FIG. 1 also shows two distal screw holes 10a and 10b in rod 10 which are to be targeted, as well as a magnetic positioning device generally denoted 14 and described in more detail below.

Figure 2:
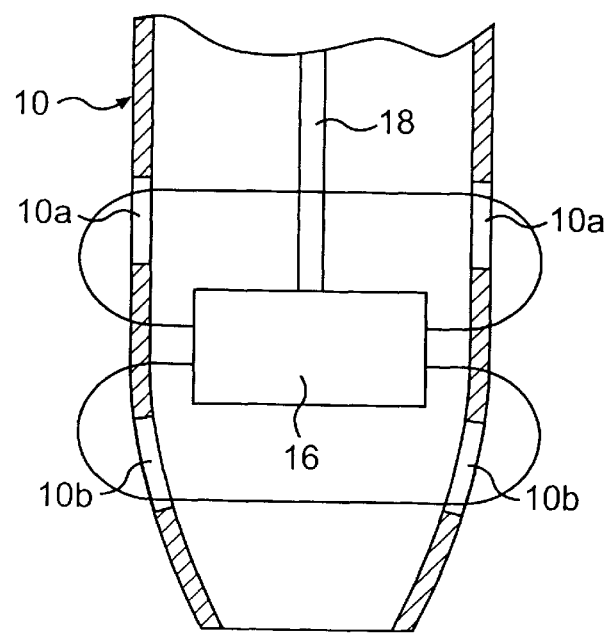
FIG. 2 is a cross sectional view of the distal end portion of the rod of FIG. 1, showing a target magnet sited therein.

Referring to FIG. 2, there is shown, to an enlarged scale, the distal end of locking rod 10, illustrating the proximal transverse screw hole 10a and distal transverse screw hole 10b. A magnet 16 on the distal end of an elongate magnet positioning rod or wand 18 is placed in rod 10 so as to extend parallel to, and just proximal of, the hole to be drilled, viz, in this case, distal target hole 10b.

Figure 3:
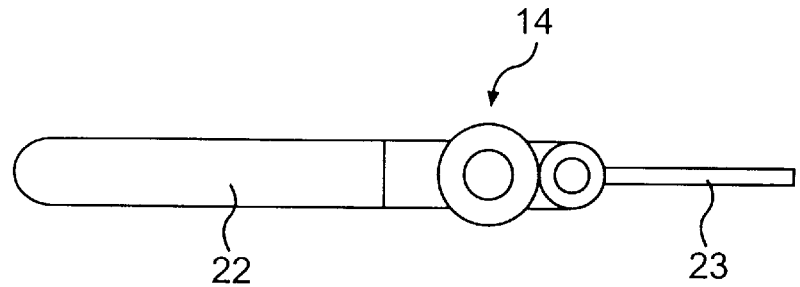
FIGS. 3 and 4 are top plan and side elevational views, respectively, of the magnetic positioning guide device of FIG. 1, with FIG. 4 showing the device in operation.
Figure 4:
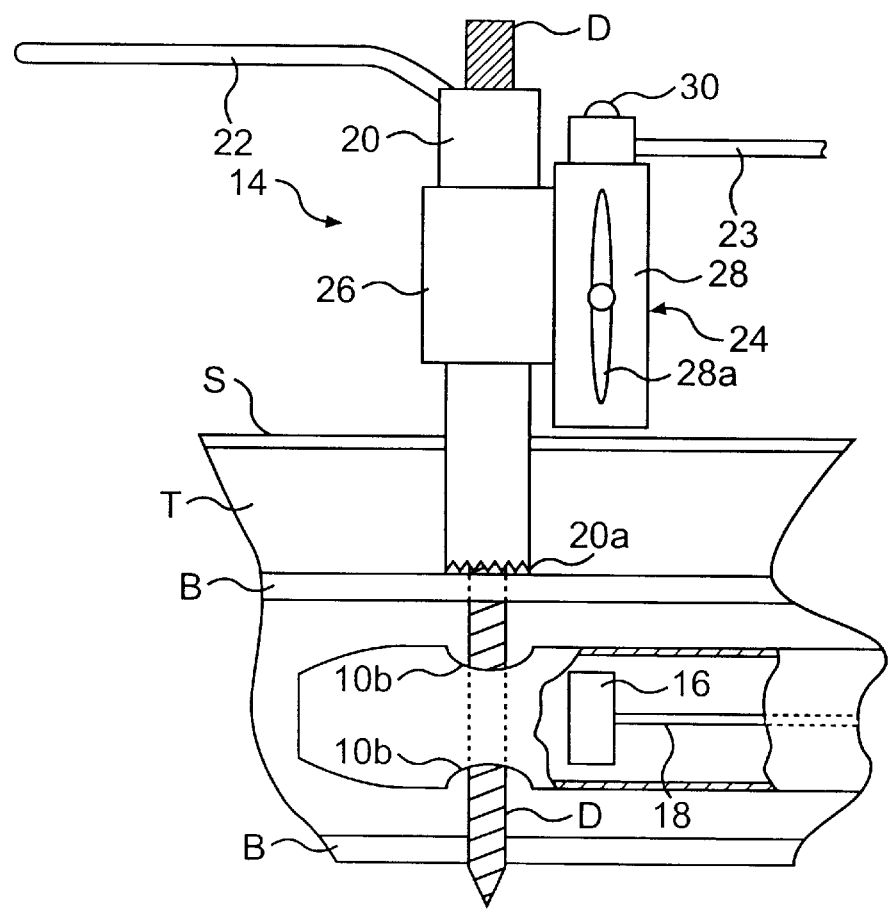

Referring to FIGS. 3 and 4, one preferred embodiment of magnetic positioning device 14 is shown. The device 14 includes a non-magnetic drill sleeve 20 in the form of a hollow cylinder through which, as shown in FIG. 4, a drill D is inserted. A control handle 22 is affixed to sleeve 20 and while an alignment arm 23, described in more detail below, is used in cooperation with alignment rod 12a to provide a preliminary alignment of the magnetic positioning device 14. A magnetic compass targeter unit 24 is mounted on sleeve 20 by a cylindrical mounting element (mounting sleeve) 26 which surrounds and slides along drill sleeve 20 and which is splined thereto so that mounting element 26 is prevented from rotating about drill sleeve 20. The targeter unit 24 also includes a simple magnetic compass 28, including a compass needle 28a, such as is used for navigation, and an indicator device 30, which is shown here as an indicator lamp but which could be a buzzer or other indicator. Unit 24 includes the aforementioned alignment arm 23 affixed thereto and also incorporates a battery, a conventional magnetic switch (not shown) and a conventional on/off switch (not shown) for activating the battery circuit including the indicator device 30. The magnetic switch senses the alignment of the compass needle 28a and when the needle 28a is aligned, produces an output signal that results in activation of indicator device 30.

As is indicated schematically in FIG. 4, in the use of the device of this embodiment, an incision is made through the skin S in the soft tissue adjacent to the approximate location of the screw hole 10b to be drilled through. As indicated above in connection with FIG. 2, the magnet 16 at the distal end of the magnetic wand 18 is positioned adjacent to the distal screw hole 10b, i.e., between screw holes 10a and 10b. The drill sleeve 20 is inserted into the incision and brought into contact with the outer surface of the bone B. To this end, sleeve 20 is provided with teeth or serrations 20a at the distal end thereof for holding the drill sleeve 16 in place on bone B. Positioner 14 is adjusted in position until the needle 28a of magnetic compass 28 is aligned with magnet 16 and, at this time, a light (or audio) signal is produced by indicator device 30 which is triggered by the aforementioned magnetic switch (or, alternatively, an optical signal). With drill sleeve 20 correspondingly aligned, drill D is then drilled through the hole 10b in the intramedullary nail 10. The depth is then measured and a locking screw or pin (not shown) is inserted.

Figure 5:
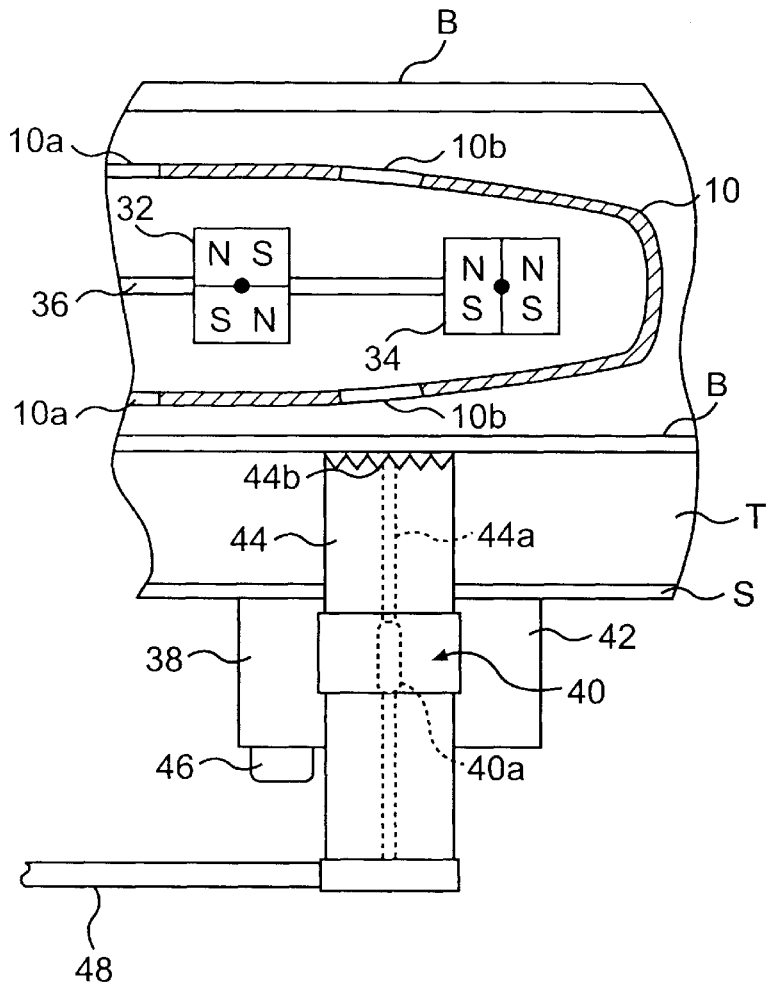
FIG. 5 is a side elevational view of a further preferred embodiment of the invention employing two magnetic switches.

Referring to FIG. 5, there is shown an alternative preferred embodiment of the invention. In this embodiment, the magnet 16 and wand 18 of FIGS. 2 and 4 are replaced by a pair of magnet devices 32 and 34 secured to a wand 36 at longitudinally spaced locations therealong. The magnet device 32 comprises a pair of conventional adjacently disposed, magnetically opposed magnets having a single axis while magnet device 34 comprises a pair of adjacently disposed magnets of like polarity. Magnet devices 32 and 34 respectively cooperate with an x-axis magnetic switch 38 and a y-axis switch 42 described further below. Such magnetic switch devices are of two general types, one wherein the device determines the central portion of a sensed magnetic field, i.e., the confluence of opposed magnets (as represented by magnets 32), and switches in response thereto, and one wherein the device switches when the sensed magnetic field passes through a maximum or central peak value (as produced by magnets 34). In the illustrated embodiment the wand 36 is first moved so that the two magnet devices 32 and 34 are first on opposite sides of the distal screw hole 10b.

The aforementioned x-axis magnet switch 38 is located on one side of a movable sleeve 40 while the aforementioned y-axis switch 43 is located on the opposite side of sleeve 40. Sleeve 40 slides on a tubular or cylindrical body member or drill sleeve 44 so that switches 38 and 40 can be brought into contact with the skin S. This minimizes the distance between the switches 38 and 40 and the sensed magnetic field produced by the respective magnet devices 32 and 34 (as described above for magnetic detector unit 24 of FIGS. 3 and 4). An indicator device 46, which can be a visual or audible device, is connected to the x- and y-switches 38 and 42 and mounted so as to move with sleeve 40. The latter is splined to tubular body member 44 by an inward projection or spline 40a received in a recess 44a in member 44 so as to enable longitudinal movement of sleeve 40 while preventing rotation thereof. A serrated edge 44b provides secure engagement of the tubular body member 10 with the bone B. A drill guide handle 48 is affixed or connected to the opposite end of tubular body member 44.

It will be appreciated that the operation of the embodiment of FIG. 5 is similar to that of FIGS. 3 and 4 and that the two embodiments are similar apart from the kind of magnetic sensing that is used. In the embodiment of FIG. 5, when both of the x- and y-axis switches 38 and 42 are properly aligned, and actuated, indicator 46 is triggered and a suitable indication (e.g., a light or audible buzzer) is produced. The drill hole is then made via tubular body member 44, through the distal hole 10b. The magnet carrying wand 36 is moved proximally so as to be out of the way, and so as to position the magnets 32 and 34 on opposite sides of the proximal hole 10a, and the locking screw (not shown) is inserted. The process is then repeated for proximal hole 10a.

Figure 6:
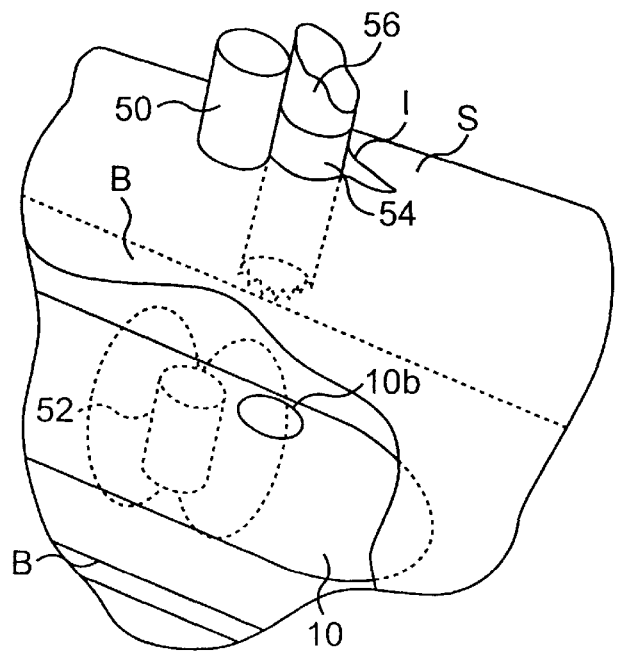
FIG. 6 is a highly schematic perspective view of a further preferred embodiment of the invention employing a single magnetic switch.

Referring to FIG. 6, there is shown a high schematic perspective view of a further preferred embodiment of the invention. This embodiment is similar to that of FIG. 5 but differs in that only a single magnetic switch 50 is used which senses the location of a single magnet or magnet device 52 within an intramedullary nail 10 proximal of and adjacent to a locking hole 10b. Magnetic switch 50 is mounted by a sleeve 54 on a drill guide member 56. As described above, magnetic switch 50 is slid down member 56 to a position in contact with the skin S while member 56 itself is inserted through an incision I to a position wherein the distal end contacts the bone B. As indicated above, target magnet 52 is positioned just proximal to the distal transverse locking hole 10b and when the magnetic switch 50 is directly over the magnetic axis of magnet 52, switch 50 is triggered and an indicator device (not shown) produces a visual or audible output which signals alignment. As described above for the other embodiments, a hole is then drilled by a drill (not shown in FIG. 6) through hole 10b and a correct length screw is inserted.

It will be understood that placing of a magnet proximal to the screw hole eliminates the need for guide wire such as is used in the prior art devices discussed above. Further, with the use of a magnetic switch or switches or a small compass or other balance finder with reduced mass as compared with prior art magnetic balance finders, increased sensitivity can be provided at lower cost while still permitting percutaneous drilling without using a pre-existing guide wire. When only one magnetic switch is used, the precise drilling angle is more difficult to determine, and a visual reference guide (e.g., the rod or arm 12a extending down from the proximal handle of the nail 12 as described above) may be useful in providing preliminary alignment of the drill guide unit. A further advantage of the invention is that the magnetic detector(s) of the finder unit (whether a magnetic switch or switches or a magnetic compass) can be reused and that the only disposable portion of the overall system or assembly is the magnet or magnets at the end of the wand which is inserted down the intramedullary nail.

Figure 7:
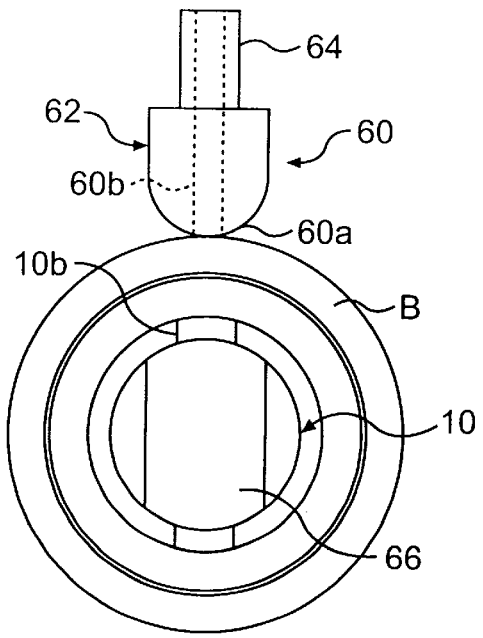
FIG. 7 is a side elevational view of a further embodiment of a magnetic positioning guide device or system in accordance with a further aspect of the invention.

Referring to FIG. 7, a further embodiment of the invention is shown. This embodiment is an inexpensive, simple alternative to the embodiments described above (and, more importantly, to the prior art devices described previously) and is believed to be particularly applicable to smaller bones wherein the targeting distances are small. In this embodiment, a very lightweight cannulated targeting magnet device 60 is used which includes a magnet 62 having a rounded bottom or "rocker" surface 60a and including a channel or drill hole 60b therein and a short drill guide tube 64 secured to the magnet 62 in order to enable a drill to be inserted through the targeting device 60. A cooperating target magnet 66 is located at a selected hole, denoted 10b, in a intramedullary rod or nail 10 in the intramedullary canal in a bone B. The magnetic targeting device 60 is constructed so as to be light enough in weight that the magnet 62 will rock or pivot about surface 62a so as to automatically line up on the surface of the bone B perpendicular to the magnetic field and thus allow a pin or screw to be drilled directly along the axis of the magnetic field. The device 60 should be useful with small bones such as forearm bones, fibulas or even small metacarpal bones, and requires that the respective magnets 62 and 66 be located very close together so that the force of the magnetic field overcomes the weight of the magnet device and so that the rocker bottom 62a of magnet 62 can act essentially as a universal pivot.

Figure 8:
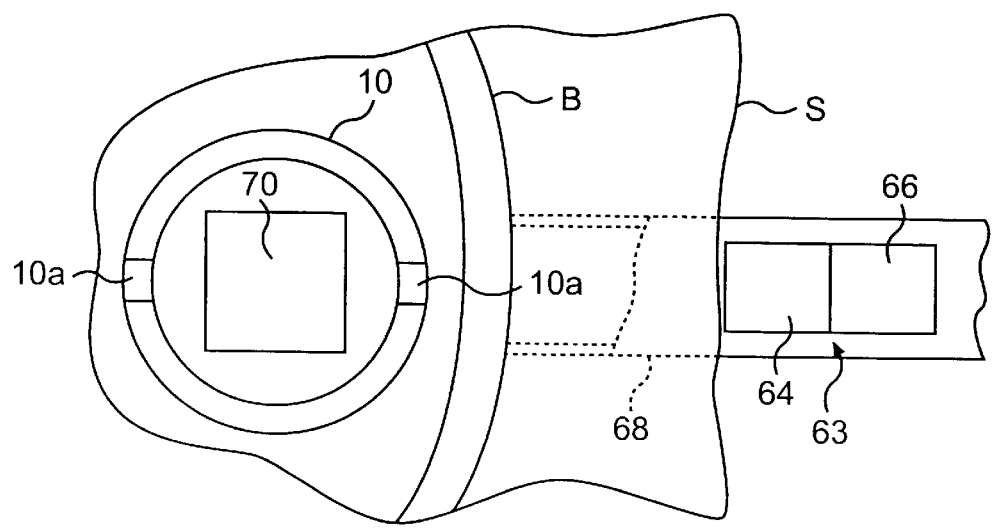
FIG. 8 is a schematic top plan view of a device in accordance with a further preferred embodiment of the invention, showing the device in use.
Figure 9:
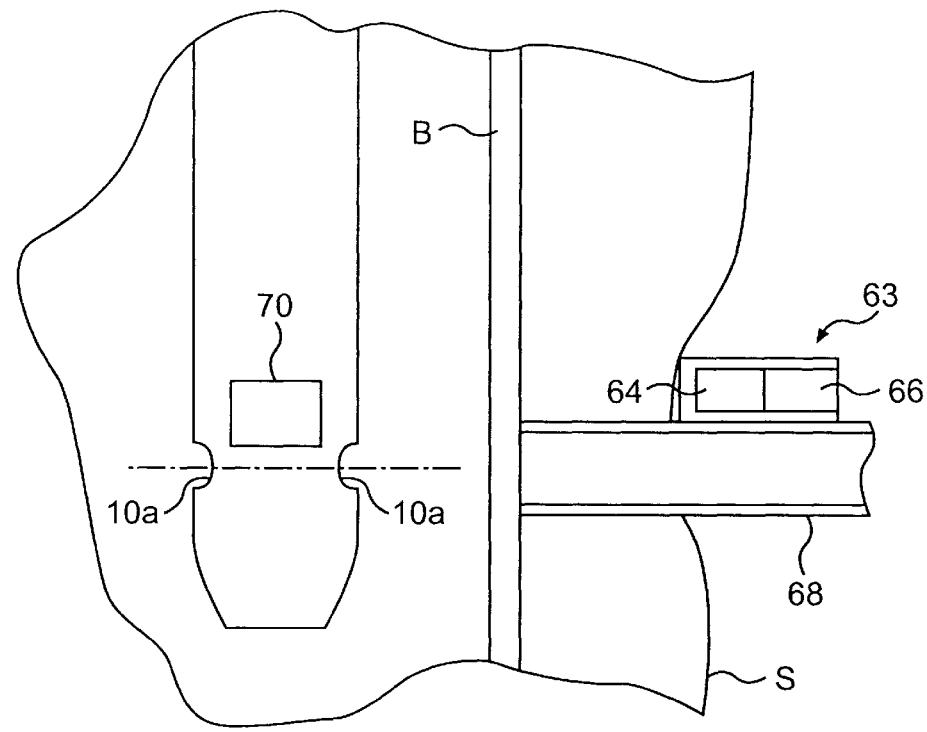
FIG. 9 is a schematic side elevational view of the embodiment of FIG. 8 also showing the device in use.

Referring to FIGS. 8 and 9, yet another embodiment of the invention is shown. In this embodiment, a combination or assembly 63 of a sensor or seeker magnet 64 and a strain gauge 66 is mounted on a cylindrical drill guide 68. A target magnet 70 is located within an intramedullary rod 10 in proximity to but spaced from transverse locking screw holes 10a. The magnet-strain gauge assembly 63 is mounted on drill guide 68 in axially offset relation so that when seeker magnet 66 is aligned with target magnet 70, drill guide 68 is aligned with screw holes 10a (in common with some of the embodiments discussed above). In this embodiment, the drill guide 68 is brought into contact with the bone B and the assembly 63 is brought into contact with the skin S. The strain gauge 66 is used to determine this alignment as discussed below.

Figure 10:
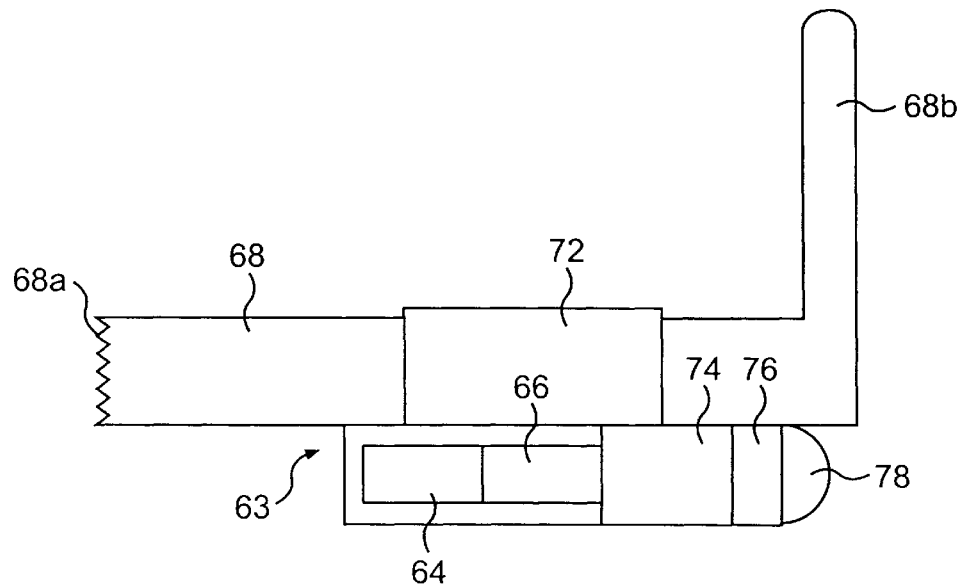
FIG. 10 is a side elevational view of the device of FIGS. 8 and 9, showing further details of a preferred implementation thereof.

Further details of this embodiment of the invention are illustrated in FIG. 10. This embodiment is similar to that of FIG. 4 and, in this regard, the sensor or seeker magnet 64 and strain gauge 66 are mounted on a slide 72 on drill guide 68 so that the magnet-strain gauge assembly 63 can be brought into contact with the skin. Similarly to the embodiment of FIG. 4, drill guide 68 preferably includes gripping teeth 68a at the distal end and a control handle 68b. A logic circuit 74 connected to strain gauge 66 controls actuation of an indicator device 78 which is shown as an indicator lamp but can comprise any suitable kind of audible or visual indicator. A battery 76 is provided as a power supply for the electrical system including logic circuit 74 and indicator lamp 78.

Figure 11:
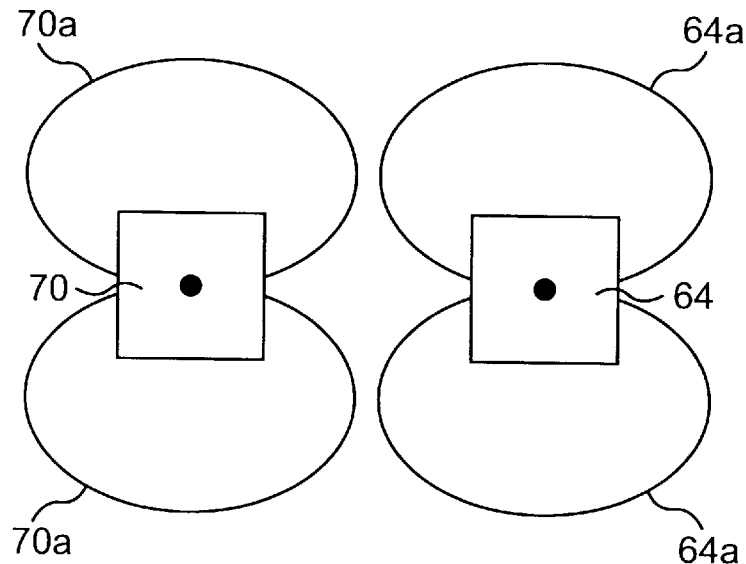
FIGS. 11 and 12 are diagrams used in explanation of the operation of the device of FIGS. 8 to 10.
Figure 12:
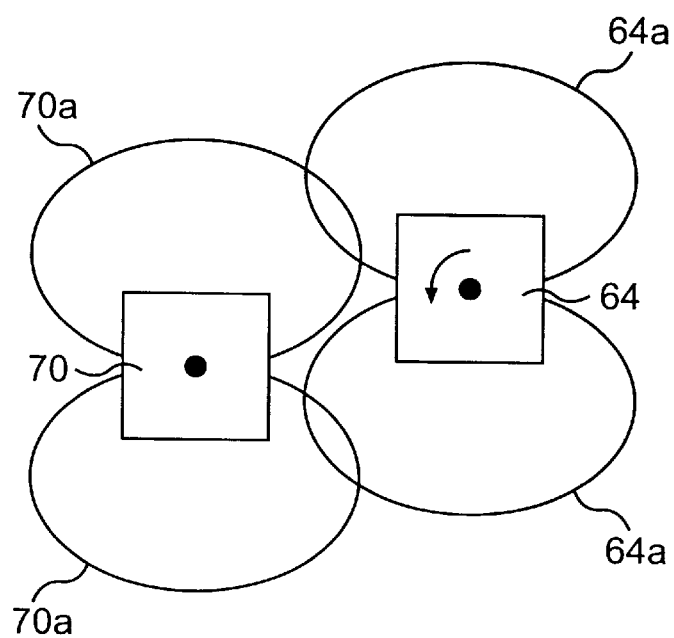

Turning to the operation of strain gauge 66, strain gauge 66 can be a piezoelectric strain gauge or a mechanical strain gauge, it being noted that strain gauges can be made very small and that some three-dimensional piezoelectric strain gauges are only about ¼ to ⅜ inch in size (which is about the size of a small seeker magnet). In general, strain gauge 66 detects a torque exerted on the seeker magnet 64 affixed thereto when magnet 64 is out of alignment therewith. This mode of operation is illustrated in a schematic manner in FIGS. 11 and 12. Referring first to FIG. 11, when the magnets 70 and 64 are aligned, the corresponding flux lines 70a and 64a are symmetrical and the x- and y-axis flux values should be equal and the z-axis flux value should be a maximum. This is detected by logic circuit 76 which actuates indicator 78 to provide an audible and/or visible signal that alignment has been effected. Referring to FIG. 12, if the magnets 64 and 70 are not aligned, a torque is exerted on the seeker magnet 64 and there are unequal x-and y-axis flux values and the z-axis flux value is not at a maximum.

Although in the embodiment of FIGS. 8 to 10 an offset or adjacent (non-cannulated) magnet arrangement is used, an axial or cannulated embodiment can also be employed. This embodiment, which is not illustrated, would use a cannulated magnet and, for example, a series of mechanical piezoelectric strain gauges arranged in an annular configuration. Further, although a percutaneous embodiment has been described, the magnet-strain gauge unit could be arranged to slide down to bone where necessary to provide increased sensitivity. Further, it will be appreciated that both attractive and repulsive magnetic arrangements can be used.

Although the invention has been described above in relation to preferred embodiments thereof, it will be understood by those skilled in the art that variations and modifications can be effected in these preferred embodiments without departing from the scope and spirit of the invention.

What is claimed is:

1. A device for targeting transverse locking holes for locking screws or pins in an elongate hollow orthopedic locking element, the locking element including a longitudinal bore and being inserted, in use, within a bone of a patient so as to fix the bone, and said device comprising:

a tubular drill guide member having an axial drill guide bore extending therethrough for receiving a drill for, when aligned with a target locking hole, drilling through the bone via the target locking hole, said guide member having a distal end adapted to be brought into contact with the bone;

at least one target magnet adapted to be inserted into the longitudinal bore in the locking element to a position adjacent to, and offset from, the target locking hole;

magnetic targeting means, mounted for movement on said drill guide member and disposed in laterally offset relation to said axial drill guide bore so as to produce a maximum output in response to sensing a magnetic field laterally offset from the axial drill guide bore, for sensing the offset location of the at least one target magnet with respect to the target locking hole and for producing said output when said magnetic targeting means is aligned with the at least one target magnet at said offset location and thus said drill guide bore is aligned with the target locking hole; and indicator means for, responsive to said output, indicating when said magnetic targeting means is aligned with said at least one target magnet at said offset location and thus indicating that said drill guide bore is aligned with the target locking hole.

2. A device for targeting transverse locking holes according to claim 1 further comprising a movable sleeve mounted on said guide member, carrying said magnetic targeting means, and movable to a position wherein said magnetic targeting means is brought into contact with an area of skin overlying the bone.

3. A device for targeting transverse locking holes according to claim 2 further comprising a spline connection between said sleeve and said drill guide member for preventing rotation of said sleeve on said drill guide member.

4. A device for targeting transverse locking holes according to claim 1 wherein said magnetic targeting means comprises a magnetic balance finder having a movable element which assumes a predetermined orientation when aligned with the at least one target magnet.

5. A device for targeting transverse locking holes according to claim 1 wherein said distal end of said drill guide member includes teeth for holding said drill guide member in contact with the bone.

6. A device for targeting transverse locking holes according to claim 5 wherein said at least one pair of magnets comprises first and second magnets of like polarity disposed in side by side relation.

7. A device for targeting transverse locking holes according to claim 5 wherein said at least one pair of magnets comprises first and second permanent magnets of opposite polarity disposed in side by side relation and third and fourth permanent magnets of like polarity disposed in side by side relation and spaced from said first and second magnets.

8. A device for targeting transverse locking holes according to claim 1 wherein said magnetic targeting means comprises a magnetic compass having a movable pointer, a sensor for sensing the position of said pointer and for producing a trigger signal when said pointer assumes a predetermined position and an indicator device activated by said trigger signal.

9. A device for targeting transverse locking holes according to claims 8 wherein said sensor comprises a magnetic switch.

10. A device for targeting transverse locking holes according to claim 8 wherein said indicator device comprises an indicator lamp.

11. A device for targeting transverse locking holes according to claim 8 wherein said magnetic targeting means further comprises a control handle affixed to said guide member.

12. A device for targeting transverse locking holes according to claim 8 wherein the at least one target magnet comprises a target magnet located at one end of a wand member.

13. A device for targeting transverse locking holes according to claim 8 wherein said magnetic targeting means further comprises an alignment arm extending transverse to said drill guide member for assisting in providing preliminary alignment of said magnetic targeting means.

14. A device for targeting transverse locking holes according to claim 13 wherein the orthopedic locking element includes a U-shaped handle having an external leg extending substantially parallel to said longitudinal bore and an axial alignment element extending axially from said external arm for alignment with said alignment arm.

15. A device for targeting transverse locking holes according to claim 1 wherein said magnetic targeting means comprises a magnetic switch for producing a triggering signal when said magnetic switch is in alignment with the at least one target magnet.

16. A device for targeting transverse locking holes according to claim 15 further comprising a movable sleeve mounted on said drill guide member, carrying said magnetic switch and movable to a position wherein said magnetic switch is brought into contact with an area of skin overlying the bone.

17. A device for targeting transverse locking holes according to claim 1 wherein the at least one target magnet comprises first and second spaced magnet devices for producing respective magnetic fields, and said magnetic targeting means comprises a first x-axis magnetic switch for detecting the magnetic field produced by the first magnet device and a second y-axis magnetic switch for sensing the magnetic field produced by the second magnet device.

18. A device for targeting transverse locking holes according to claim 1 wherein the at least one target magnet comprises at least one pair of adjacently disposed magnets for producing a resultant magnetic field, and said magnetic targeting means comprises at least one magnetic switch for producing a triggering signal response to detecting a predetermined characteristic of said resultant magnetic field.

19. A device for targeting transverse locking holes according to claim 18 wherein said at least one pair of magnets comprises first and second permanent magnets of opposite polarity disposed in side by side relation.

20. A device for targeting transverse locking holes according to claim 1 wherein said magnetic targeting means comprising a sensor magnet and a strain gauge for sensing the torque exerted on the sensor magnet by the target magnet.

21. A device for targeting transverse locking holes for locking screws or pins in an elongate hollow orthopedic locking element, the locking element including a longitudinal bore and being inserted, in use, within a bone of a patient so as to fix the bone, and said device comprising:

a tubular drill guide member having a drill guide bore therethrough for receiving a drill for, when aligned with a target locking hole, drilling through the bone via the target locking hole, said guide member having a distal end adapted to be brought into contact with the bone;

at least one target magnet for producing a magnetic flux field and adapted to be inserted into the longitudinal bore in the locking element to a predetermined position with respect to the target locking hole; and magnetic targeting means, mounted for movement on said drill guide member, for sensing the location of the at least one target magnet and for producing an output when said magnetic targeting means is aligned with the at least one target magnet, said magnetic targeting means comprising a sensor magnet for producing a magnetic flux field which, in use of the device, interacts with the flux field of the at least one target magnet, and a strain gauge for sensing strain on said sensor magnet produced by interaction of said magnetic flux fields and for producing a corresponding output.

22. A device for targeting transverse locking holes according to claim 21 wherein said sensor magnet comprises a permanent magnet of fixed strength and polarity.

23. A device for targeting transverse locking holes in a hollow elongate orthopedic locking element including a longitudinal bore therein and adapted to be located, in use, within a bone of a patient, and thus enabling locking screws to be inserted into said holes, said device comprising:

a target magnet adapted to be inserted into the locking element at a target locking hole; and a cannulated targeting magnet comprising a permanent magnet having a rounded bottom surface about which the permanent magnet pivots and adapted to be placed, in use, into pivotable contact with a surface of the bone so as to be brought into alignment with said target magnet, said cannulated targeting magnet having a drill guide passage therethrough for receiving a drill for, when said targeting magnet is aligned with the target magnet at the target locking hole, drilling through the bone via the target locking hole.

24. A device for targeting transverse locking holes for locking screws or pins in an elongate hollow orthopedic locking element, the locking element further including a longitudinal bore and being inserted, in use, within a bone of a patient so as to fix the bone, and said device comprising:

a tubular drill guide member having a drill guide bore therethrough for receiving a drill for, when aligned with a target locking hole, drilling through the bone via the target locking hole, said guide member having a distal end adapted to be brought into contact with the bone;

at least one target magnet adapted to be inserted into the longitudinal bore in the locking element to a position adjacent to, and proximally offset from, the target locking hole; and magnetic targeting means, mounted for movement on said drill guide member in laterally offset relation to said drill guide bore, for sensing the location of the at least one target magnet and for producing an output when said magnetic targeting means is aligned with the at least one target magnet and thus said drill guide bore is aligned with the target locking hole, said magnetic targeting means comprising a magnetic switch for producing a triggering signal when said magnetic switch is in alignment with the at least one target magnet.

* * * * *